United States Patent [19]

Kirchner

[11] Patent Number: 4,561,437
[45] Date of Patent: Dec. 31, 1985

[54] TENSIONING DEVICE, PARTICULARLY FOR TIGHTENING BANDS IN MEDICAL PRACTICE

[75] Inventor: Hansjörg Kirchner, Markgroningen, Fed. Rep. of Germany

[73] Assignee: Kirchner & Wilhelm, Fed. Rep. of Germany

[21] Appl. No.: 606,373

[22] Filed: May 2, 1984

[30] Foreign Application Priority Data

May 7, 1983 [DE] Fed. Rep. of Germany ....... 3316758

[51] Int. Cl.⁴ .............................................. A61L 17/00
[52] U.S. Cl. ................................. 128/327; 24/16 PB; 24/115 H; 24/170
[58] Field of Search ............... 128/327, 346, 325, 326; 24/115 H, 115 K, 133, 132 AA, 134 KA, 134 KB, 134 R, 132 R, 16 PB, 688, 543, 170, 191, 481, 484

[56] References Cited

U.S. PATENT DOCUMENTS

| | | | |
|---|---|---|---|
| 1,751,850 | 3/1930 | Zieburtz | 24/133 |
| 2,882,903 | 4/1959 | Ramien | 128/327 |
| 3,958,575 | 5/1976 | Von Soiron | 128/327 |
| 4,102,343 | 7/1978 | Schneider | 128/327 |

Primary Examiner—John J. Wilson
Assistant Examiner—John G. Weiss
Attorney, Agent, or Firm—McGlew and Tuttle

[57] ABSTRACT

A device for applying tension around an object such as a person's arm and leg comprises a tensioning member which has a first end portion which is connected to a rear end of a hollow basic member housing and includes a portion adapted to form an object encircling loop for engagement, for example around a person's arm and has a second opposite free end portion. The hollow basic member has a rear end wall with an entrance opening and a front end wall with an exit opening to facilitate passage of the free end portion of the tensioning member into the entrance opening through the hollow member and out the exit opening. The interior of the basic member includes a backup portion which has a backup surface over which the free end portion of the tensioning member is passed. A lever pressure member is pivotally mounted in the basic member and it overlies the free end portion of the tensioning member and is pivotable about a horizontal axis and includes a first arm portion which overlies the tensioning member and has an opening therethrough for the passage of the tensioning member as it exits through the exit opening of the basic member. The tensioning member bears against the first arm portion of the lever and the construction is such that the lever member holds the tensioning member after it has been applied around the object and tensioned on the backup surface. The lever member may be pivoted by engaging a release button portion of the first arm which extends through the exit opening and has an opening therethrough for the passage of the tensioning member thereover. The lifting of the button member frees the tensioning member so that it can be released from tensioning engagement.

8 Claims, 1 Drawing Figure

U.S. Patent Dec. 31, 1985 4,561,437
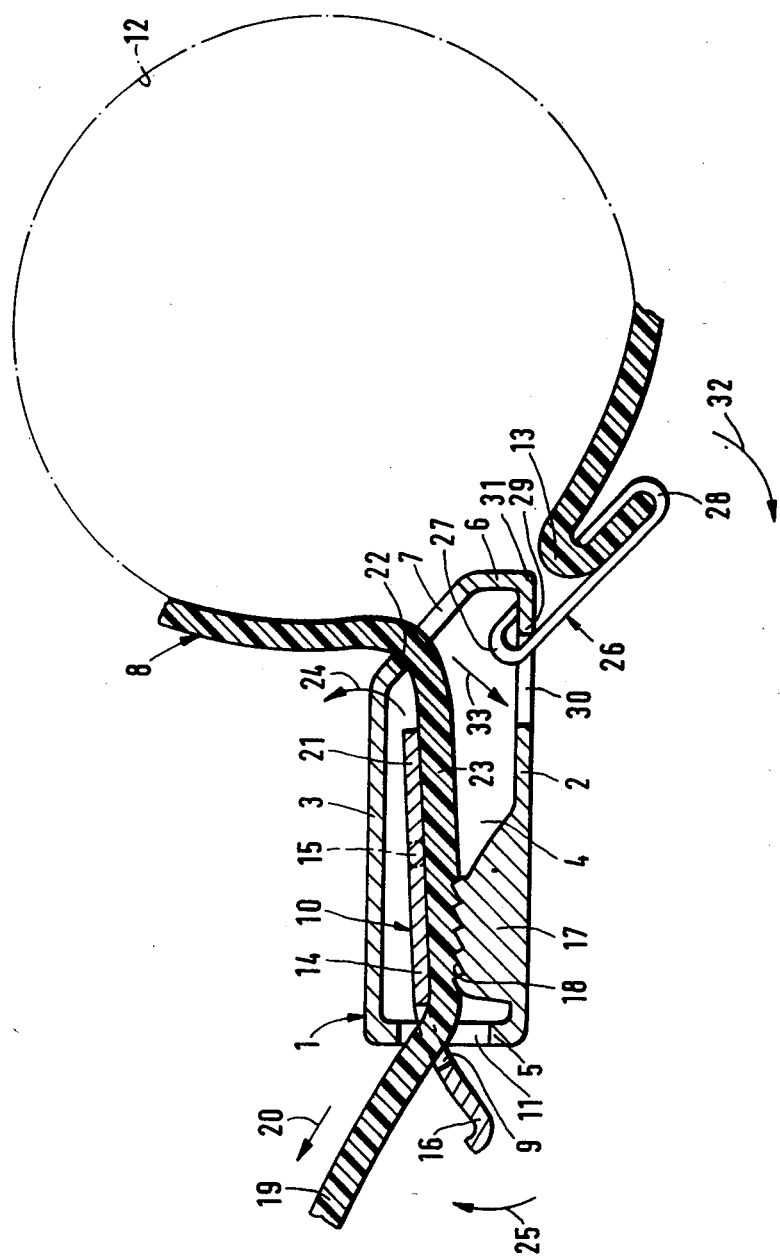

TENSIONING DEVICE, PARTICULARLY FOR TIGHTENING BANDS IN MEDICAL PRACTICE

FIELD AND BACKGROUND OF THE INVENTION

This invention relates in general to medical devices and in particular to a new and useful device for applying tension on an object such as a person's arm and leg.

A prior art device of this kind comprises a basic body which is open in the direction of the pivotal axis of its pressure member, so that the tightening member can easily be introduced and removed. The tensioning device thus can be rapidly applied and released again, after a blood pressure reading, for example. However, the device requires a spring-loaded pressure member making sure that in released state, the tightening member will not unintentionally slip out of the basic body.

A loading spring is easily a source of troubles and increases manufacturing costs.

SUMMARY OF THE INVENTION

The invention is directed to an improved tensioning device permitting the omission of the loading spring.

In accordance with the invention, a device for applying tension around an object such as a person's arm and leg includes a tensioning member which has a first end portion which is connected to a rear end of a hollow basic member housing and includes a portion adapted to form an object encircling loop for engagement, for example around a person's arm and has a second opposite free end portion. The hollow basic member has a rear end wall with an entrance opening and a front end wall with an exit opening to facilitate passage of the free end portion of the tensioning member into the entrance opening through the hollow member and out the exit opening. The interior of the basic member includes a backup portion which has a backup surface over which the free end portion of the tensioning member is passed. A lever pressure member is pivotally mounted in the basic member and it overlies the free end portion of the tensioning member and is pivotable about a horizontal axis and includes a first arm portion which overlies the tensioning member and has an opening therethrough for the passage of the tensioning member as it exits through the exit opening of the basic member. The tensioning member bears against the first arm portion of the lever and the construction is such that the lever member holds the tensioning member after it has been applied around the object and tensioned on the backup surface. The lever member may be pivoted by engaging a release button portion of the first arm which extends through the exit opening and has an opening therethrough for the passage of the tensioning member thereover. The lifting of the button member frees the tensioning member so that it can be released from tensioning engagement.

In this design, the tightening member is passed through the basic body, which is known per se. Only known designs have the drawback that upon terminating the measurement, the loop must be enlarged in a complicated manner and against the action of a spring, to be able to withdraw an arm or leg. In the inventive device, the loop becomes free to enlarge in a simple way, by actuating a release button. With the button pressed, the loop enlarges merely under the applied pull so that the released extremity is easily withdrawn therefrom. If necessary, the loop may further be enlarged by additional pulling at the basic body. The tightening member becomes clamped merely by producing a tension therein. This tension produces a torque at the lever arm close to the loop, of the pressure member, by which the tightening member portion remote from the loop is pressed by the other lever arm against the firm backup surface provided in the basic body. An end portion of the tightening member still protrudes out of the basic body, so that to release the tightening member again, the protruding portion may be slightly lifted, to enable the portion hitherto clamped between the lever arm and the backup surface to slip through until the tension of elastically stretchable tightening member is completely released. Additional retracting, i.e. enlarging of the loop, as already mentioned, is easily possible by pulling at the loop, or at the basic body.

The basic body is advantageously a flat rectangular hollow body having an oblique entrance end portion with the entrance opening for the passage of the tensioning member at the location of one end of the loop. The opposite end of the loop is secured by a C-shaped anchoring device which engages through an opening in the bottom wall of the basic body and holds this first end of the tensioning member to the basic body. The construction of the basic body is such that it forms a continuation of the loop's circumferential formation.

This direction refers to the applied and tensioned tightening member. The oblique portion of the basic body bridges the gap between the respective two opposite portions of the substantially annular loop. The height of the basic body is determined by the thicknesses of the tightening member and the pressure member, by the level of the backup surface, and by the pivotal angle of the pressure member. Its width exceeds that of the tightening member by the necessary wall thicknesses. With the tightening member tensioned, the oblique surface of the basic body applies against the patient's extremity, for example, arm, in a position intermediate between radial and tangential. Since the release button is provided at the basic body end remote from the loop, it is particularly well accessible in this oblique position.

A pressure lever member advantageously includes a transverse slot located in the zone of the exit opening of the basic member so that the tensioning member may pass both through the opening and the slot of the lever member to the exterior of the basic member.

The pressure lever member has substantially the shape of a plate which in the area of the transverse slot is angled or bent toward the backup surface located in the basic body. A pressure member in the associated section of the tightening member thus cross in the zone of the transverse slot.

When the loop of the tensioning member is under tensioning pressure the arm portion of the lever member is spaced from the bottom of the basic member less than the second arm portion of the pressure member.

While taking a certain tension in the loop as the basic, the pivotal position of the pressure member in the housing and thus also its association with the bottom of the housing is to some extent accurately defined. With the bottom of the basic body taken as the reference base, the upper edge of the passage aperture extending at angle of approximately 40° to 50° is slightly remoter than the pressure member and at the loop side, so that the tensioned tightening member produces a torque at this lever arm of the pressure member. This torque presses the opposite lever arm, thus the pressure member against the backup surface which is fixed to the basic body. In a manner known per se, the backup surface is roughened, grooved, knurled, or the like, so that an elastic tightening member made of a belt material, for example, is securely clamped.

Advantageously, the first end of the tensioning member is detachably secured to the basic member by a C-shaped securing piece. This is advantageous for the manufacture, and provides for another way of releasing a tensioned tightening member. Here again, the tension in the tightening member is advantageously utilized, since upon being disengaged from the basic body, the tightening member jumps resiliently away from the arm, etc., automatically and quickly. This makes unnecessary a withdrawing of the arm, etc., which cannot be avoided with a firm securing of the respective end of the tightening member to the basic body.

The C-shaped member engages through a slot defined in the bottom of the basic member and has a curved end which engages around the bottom wall of the basic member. One end of the C-shaped member forms an engaging hook engaged in the basic member and the other end forms a retaining element which engages the first end of the tensioning member. This has two advantages: the anchoring piece is prevented from directly contacting the arm, etc., and the spacing between the tightening member and the basic body is minimized so that a pinching of the patient's skin is avoided, and the C-shaped leg holding the tightening member makes it possible to quickly disengage the other hook from the basic body. The elasticity of the tightening member is advantageously utilized for this purpose, that is, if the anchoring piece which, in its engaged position, extends obliquely away from the bottom of the basic body, is swung through about 90° toward the bottom of the basic body, the C-leg held by the basic body becomes unlocked and the pull of the loop instantly disengages this leg, since due to the swing, the anchoring piece comes into a favorable release position for slipping out over the retaining edge.

Accordingly, it is an object of the invention to provide an improved tensioning member with a flexible tensioning element is engaged around an object and is held at one end to a hollow basic member which has an opening at each end for the passage of the tensioning member therethrough and which also includes a pivotal lever member which holds the tensioning member under tension against the backup surface, but which may be relieved by pivoting it to release the tensioning member.

A further object of the invention is to provide a tensioning device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a longitudinal sectional view of a tensioning device constructed in accordance with the invention.

DESCRIPTION OF THE PREFERRED EMBODIMENT

Referring to the drawing in particular, the invention embodied therein comprises a device for applying tension around an object such as a person's arm or leg and it comprises a tensioning member 8 which has a first end portion 13, a portion adapted to form an object encircling loop 12 and a second opposite free end portion 19. A hollow basic member 1 has a rear end wall 6 with an entrance opening 7 and a front end wall 5 with an exit opening 11 through which the free end portion is passed. The basic member includes a backup portion 17 therein which has a backup surface 18 over which the free end portion 19 of the tensioning member is passed. In accordance with a feature of the invention a lever pressure member 10 is pivotally mounted in the basic member 1 for pivotal movement about a horizontally disposed pivot pin 15. The lever pressure member 10 overlies a portion of the free end 19 of the tensioning member and it has a first arm portion 14 located adjacent the exit opening with a passage or opening 9 therethrough which is adjacent the exit opening 11 through which the free end portion 19 of the tensioning member 8 extends. Pressure lever member 10 also includes a second arm portion which overlies a portion of the free end 19 of the tensioning member and a pressure lever arm member 10 aids in holding the tensioning member after it has been tensioned so that it overlies the backup surface 18 and is held thereby. A pressure lever member 10 includes a release button portion 16 which extends exteriorally of the basic member which may be engaged to lift the first arm portion to release the tensioning from the tensioning member 8. The tensioning member 8 is advantageously held to the basic member 1 by means of a C-shaped clamp 26 which engages through a slot 30 in a bottom wall 2 of the basic member 1 and includes an engaging hook 27 at one end which engages over a ledge portion 29 and an engaging or retaining hook 28 at its opposite end which engages over the first end 13 of the tensioning member 8.

The basic body 1 of the tensioning device is a substantially rectangular hollow body comprising a bottom 2, a cover 3 parallel thereto, two parallel lengthwise side walls 4 of which only the rear wall is shown in the view, and two transverse end walls 5,6. Wall 6 extends obliquely, so that cover 3 is shorter than bottom 2. The oblique wall portion is provided with a passage aperture 7 through which the free end of the tightening member 8 extends into the interior of basic body 1. Member 8 extends through the entire body 1 and protrudes at the other side through a transverse slot 9 and a passage aperture 11 of the basic body 1. Tightening member 8 forms a loop 12 having a first end 13 detachably connected to basic body 1 as will be explained hereinafter. Transverse slot 9 is provided in a lever arm 14 remote from loop 12 of a pressure member 10 which is designed as a two-armed lever. Pressure member 10 is mounted for limited pivoting in basic body 1 by means of a shaft or two laterally projecting journal pins 15 engaging bearing holes in side walls 4. Lever arm 14 extends through the passage aperture 11 remote from the loop and its end portion protruding outside forms a release button 16.

As shown in the FIGURE, pressure member 10 is substantially plate-shaped, with a portion in the zone of transverse slot 9 bent toward bottom 2 of the basic body 1. Transverse slot 9 is provided about at the location where the pressure member 10 is bent. Further, as shown, transverse slot 9 is associated with the passage aperture 11 remote from the loop, of basic body 1. Advantageously, basic body 1 is made in two parts (not shown).

Extending from bottom 2 of basic body 1 is a back-up portion 17 having a surface 18 facing cover 3. Surface 18 is grooved, knurled, or otherwise roughened, and associated with lever arm 14 of pressure member 10, which arm is remote from loop 12. Tightening member 8 which is passed through basic body 1, extends in the gas between surface 18 and lever arm 14. By pulling member 8 by its free end 19 (shown cut off), in the direction of arrow 20, loop 12 is tensioned around the patient's arm to squeeze the patient's blood vessels.

With loop 12 tensioned, the end 21 at the loop side, of pressure member 10 is spaced from bottom 2 of body 1 less than an end 22 remote from bottom 2 of the passage aperture 7 of body 1. Consequently, portion 23 of tightening member 8 extending between aperture 7 and backup surface 18 applies against end 21 of pressure member 10, shown in the FIGURE at the right hand side, to produce a torque in the direction of arrow 24. At the same time, lever arm 14 remote from the loop is pressed against backup surface 18, and the respective portion of tightening member 8 becomes clamped between surface 18 and lever arm 14. In this way, a pull can be produced and maintained in loop 12, tightening the loop around the patient's arm.

If it is desired to release this pull, thus relieve the patient's blood vessels from squeeze, release buttom 16 is actuated in the direction of arrow 25. Then, the tension of loop 12 pulls the free end 19 of member 8 in the direction opposite to arrow 20, until the tension drops to zero.

First end 13 of tightening member 8 is connected to basic body 1 detachably. To this end, member 8 carries a substantially C-shaped anchoring piece 26. One leg of the C forms an engaging hook 27 while the other leg is used as a retaining element 28 for end 13 of member 8. With loop 12 tensioned, hook 27 engages behind an edge 29 of a slot 30 provided in bottom 2 of basic body 1. End 13 of member 8 is made conformable to the hook-shaped portion of anchoring piece 26 which has the advantage that in tensioned state, end 13 comes very close to edge 1 of basic body 1, so that the patient's skin cannot be pinched therebetween. In addition, as shown, the outer surface of body 1 conforms in the zone of its wall 6 snugly to the patient's arm. As also shown, end 13 is clamped in place.

By swinging anchoring piece 26 in the direction of arrow 32, the tension in loop 12 causes a disengagement of hook 27 about in the direction of arrow 33. This makes possible a quick release, without using release button 16. This manner of releasing has the advantage that loop 12 is opened, so that there is no need for withdrawing the arm etc., from the hook. On the other hand, if later the device is used again, hook 27 must first be engaged, which, however is an easy and quick operation. As tightening member 8 is pulled through basic body 1 in the direction of arrow 20 or in opposite direction, it is guided by passage aperture 7 of body 1 and transverse slot 9 of member 10, without being hindered in this motion.

While a specific embodiment of the invention has been shown and described in detail to illustrate the application of the principles of the invention, it will be understood that the invention may be embodied otherwise without departing from such principles.

What is claimed is:

1. A device for applying tension around an object such as a person's arm and leg, comprising a tensioning member having a first end portion, a portion adapted to form an object encircling loop, and a second opposite free end portion, a hollow basic member having a rear end wall with an entrance opening and a front end wall with an exit opening, said tensioning member free end portion extending through said entrance opening into the interior of said basic member and out through said exit opening, a backup portion defined in said basic member having a backup surface over which said tensioning member is passed, a lever pressure member pivotally mounted in said basic member over said backup surface and overlying a portion of said tensioning member and having a first arm portion located adjacent the exit opening with a passage therethrough and through which said tensioning member extends and having an opposite second arm portion overlying said tensioning member, said lever pressure member holding said tensioning member after it has been tensioned on said backup surface, said lever pressure member having a portion extending outside of said basic member forming a release button which is liftable to release said tensioning member and anchoring means connected to the first end of said tensioning member and to said basic member holding said tension member to said basic member and means securing said first end portion of said tensioning member to said hollow basic member.

2. A device according to claim 1, wherein said basic member comprises a substantially flat rectangular hollow body having an obliquely extending rear wall portion forming a circumferential continuation of said loop forming portion of said tensioning member.

3. A device according to claim 1, wherein said second arm portion of said lever pressure member has an opening in the form of a slot located in the same area as the exit opening.

4. A device according to claim 1, wherein said pressure member is in the form of a plate having an end portion extending outwardly from said basic member which is bent downwardly in the direction toward the bottom of said basic member.

5. A device according to claim 1, wherein said pressure lever member is located in said basic member so that when said tensioning member is tensioned, first arm portion of said pressure member is spaced at the bottom of said basic member by a lesser amount than said second arm portion.

6. A device according to claim 1, wherein said first end portion of said tensioning member is detachably secured to said basic body.

7. A device according to claim 1, including an anchoring piece connected to said first end portion of said tensioning member and having a first end with a hook formation engaged into said basic body bottom, said basic body bottom having a slot for the passage of said anchoring piece.

8. A device according to claim 7, wherein said anchoring piece is substantially C-shaped and includes a curved hook shaped end at each end, one of which engages through the slot of the bottom of said basic member, and the other of which engages around said first end portion of said tensioning member.

* * * * *